US005603933A

United States Patent [19]
Dwyer, IV et al.

[11] Patent Number: 5,603,933
[45] Date of Patent: Feb. 18, 1997

[54] CD4 PEPTIDES FOR BINDING TO VIRAL ENVELOPE PROTEINS

[75] Inventors: Victor A. Dwyer, IV; Jagannada K. Sastry, both of Houston; Ralph B. Arlinghaus, Bellaire; Pramod N. Nehete, Houston, all of Tex.

[73] Assignee: Board of Regents, The University of Texas, Austin, Tex.

[21] Appl. No.: 115,171

[22] Filed: Aug. 31, 1993

[51] Int. Cl.$^6$ .......................... A61K 39/00; A61K 38/07; A61K 38/08; C07K 5/11; C07K 17/00

[52] U.S. Cl. .................. 424/185.1; 530/328; 530/329; 530/330; 530/402; 514/15; 514/16; 514/17; 514/18; 435/5

[58] Field of Search .................. 424/278.1, 185.1; 514/2, 14–18; 530/300, 327, 328, 329, 330, 402; 930/320; 435/5

[56] References Cited

U.S. PATENT DOCUMENTS

| | | | |
|---|---|---|---|
| 4,474,795 | 10/1984 | Aron et al. | 514/396 |
| 4,493,795 | 1/1985 | Nestor, Jr. et al. | 530/326 |
| 4,725,669 | 2/1988 | Essex et al. | 530/322 |
| 4,818,527 | 4/1989 | Thornton et al. | 424/189.1 |
| 4,943,628 | 7/1990 | Rosen et al. | 530/326 |
| 4,983,387 | 1/1991 | Goldstein et al. | 424/188.1 |
| 5,013,548 | 5/1991 | Haynes et al. | 424/188.1 |
| 5,019,387 | 5/1991 | Haynes et al. | 424/188.1 |
| 5,030,449 | 7/1991 | Berzofsky et al. | 424/188.1 |
| 5,081,226 | 1/1992 | Berzofsky et al. | 530/324 |
| 5,128,319 | 7/1992 | Arlinghaus | 514/12 |
| 5,142,025 | 8/1992 | Putney et al. | 530/350 |
| 5,185,147 | 2/1993 | Papsidero | 424/188.1 |

FOREIGN PATENT DOCUMENTS

| | | |
|---|---|---|
| 0226513 | 12/1986 | European Pat. Off. |
| 0267802 | 5/1988 | European Pat. Off. |
| 0273716 | 7/1988 | European Pat. Off. |
| 0284587 | 9/1988 | European Pat. Off. |
| 0433242 | 6/1991 | European Pat. Off. |
| WO88/05051 | 7/1988 | WIPO |
| WO89/03844 | 5/1989 | WIPO |
| WO89/07112 | 8/1989 | WIPO |
| WO90/00901 | 2/1990 | WIPO |
| WO91/01996 | 2/1991 | WIPO |
| WO91/04051 | 4/1991 | WIPO |
| WO91/04045 | 4/1991 | WIPO |
| WO91/09869 | 7/1991 | WIPO |
| WO91/13910 | 9/1991 | WIPO |
| WO92/21377 | 12/1992 | WIPO |
| WO93/04697 | 3/1993 | WIPO |
| WO93/05812 | 4/1993 | WIPO |
| WO93/15750 | 8/1993 | WIPO |
| WO93/18055 | 9/1993 | WIPO |
| WO93/21218 | 10/1993 | WIPO |
| WO94/00488 | 1/1994 | WIPO |

OTHER PUBLICATIONS

Johnston, M. et al. Science 260:1286–1293 (1993).
Daar, E. et al. Proc. Natl. Acad. Sci. USA 87:6574–6578 (1990).
Ellis, R. W. "New Technologies for Making Vaccines" In: Vaccines, Plotkin & Mortimer Eds., W. B. Saunders Co. (1988).
Bowie, J. V. et al. Science 247:1306–1310 (1990).
Kumar, V. et al. Proc. Natl. Acad. Sci USA 87:1337–41 (1990).
Seckler, R et al. Biochemistry 25:2403–2409 (1986).
Shai, Y et al. Biochemistry 26:669–675 (1987).
Hintz, R. et al. J. Clin. Endocrinol Metab. 54(2):442–446 (1982).
Pauls, J. D. et al. Mol. Immunol. 30(8):709–719 (1993) received Jun. 3, 1993.
International Patent Application WO86/06414, published Nov. 6, 1986.
International Patent Application WO85/00807, published Feb. 28, 1985.
European Patent Application 044710, published Jan. 27, 1982.
C&EN, 65:24 (1987).
Buller et al., Nature, 328:77–79 (1987).
Barnes, Science, 236:1423–1425 (1987).
Salk, Nature, 327:473–476 (1987).
Newmark, Nature, 327:458 (1987).
Barnes, Science, 236:255–257 (1987).
Mitsuya and Broder, Nature, 325:773–778 (1987).
Modrow et al., J. Virol., 61:570–578 (1987).
Chanh et al., Embo. Journal, 5:3065–3073 (1986).
Newmark, Nature, 325:290 (1987).
Gallo, Scientific America, Jan., 1987, pp. 47–56.
Livingston and Fathman, Ann. Rev. Immunol., 5:477–501 (1987).
Milich and McLauchlan, Science, 234:1563–1566 (1986).
Walker et al., Science, 234:1563–1566 (1986).
Bloom, Nature, 327:193 (1987).
Putney et al., Science, 234:1392–1395 (1986).
Reiher et al., Proc. Natl. Acad. Sci. USA, 83:9188–9192 (1986).
Lagrain, J. Virol., 60:1141–1144 (1986).
Earl et al., Science, 234:728–731 (1986).
Maddon et al., Cell, 47:333–348 (1986).
Robey et al., Proc. Natl. Acad. Sci. USA, 83:7023–7027 (1986).
Zarling et al., Nature, 323:344–346 (1986).
Milich et al., J. Exp. Med., 164:532–547 (1986).
Kennedy et al., Science, 231:1555–1559 (1986).

(List continued on next page.)

Primary Examiner—Mary E. Mosher
Attorney, Agent, or Firm—Arnold White & Durkee

[57] ABSTRACT

Disclosed are compositions and methods for use in viral binding and inactivation and in protecting cells from viral infection, particularly, for use in protecting target human CD4$^+$ cells from infection by HIV. Peptides including short sequences from CD4 are identified as being particularly effective at binding to gp120 and inhibiting or reducing HIV infection of human CD4$^+$ cells by steric hinderance or catalytic inactivation of gp120. The invention thus encompasses improved CD4-based peptide compositions and therapeutic formulations with viral binding and HIV-inhibitory activity.

10 Claims, 2 Drawing Sheets

OTHER PUBLICATIONS

Berzofsky, Science, 229:932–940 (1985).
Hopp, Mil. Immunol., 21:13–16 (1984).
Shinnick et al., Ann. Rev. Microbiol., 37:425–446 (1983).
Hirsch and Kaplan, Scientific American, pp. 76–85 (believed to be between 1985 and 1987).
Austin American–Statesman, Mar. 26, 1987.
Wall Street Journal (undated).
Cease et al., Proc. Natl. Acad. Sci. USA. 84:4249–4253, Jun. 1987.
Putney et al., AIDS Vaccine Research and Clinical Trials, Eds. Putney, S. D. & Bolognesi, D. P., Marcel Dekker, Inc., New York and Basel, pp. 3–61. 1990.
Cease & Berzofsky, AIDS Vaccine Research and Clinical Trials, Eds. Putney, S. D. & Bolognesi, D. P., Marcel Dekker, Inc., New York and Basel, pp. 139–156. 1990.
Emini, AIDS Vaccine Research and Clinical Trials, Eds. Putney, S. D. & Bolognesi, D. P., Marcel Dekker, Inc., New York and Basel, pp. 369–378. 1990.
Kast et al., PNAS, 88:2283–2287, 1991.
Sastry & Arlinghaus, Curr. Sci., 5:699–707, 1991.
LaRosa et al., Science, 249:932–935, 1990.
Emini et al., J. Virol., 64(8):3674–3678, 1990.
Scott et al., PNAS, 87:8597–8601, 1990.
Javaherian et al., PNAS, 86:6768–6772, 1989.
Devash et al., PNAS, 87:3445–3449, 1990.
Palker et al., PNAS, 85:1932–1936, 1988.
Takahashi et al., PNAS, 85:3105–3109, 1988.
Takahashi et al., J. Exp. Med., 170:2023–2035, 1989.
Takahashi et al., J. Exp. Med., 171:571–576, 1990.
Berzofsky et al., Nature, 334:706–708, 1988.
Bevan, Nature, News and Views, 342:478–479, 1989.
Deres et al., Nature, 342:561–564, 1989.
Cleric et al., Nature, 339:383–385, 1989.
Howell et al., Science, 246:668–670, 1989.
Arthur et al., J. Virol. 63(12):5046–5053, 1989.
Bio/Technology, In the News, 6:345, 1988.
Barnes, Science, Research News, 242:515, 1988.
Barnes, Science, Research News, 241:533–534, 1988.
Takeda et al., Science, 242:580–583, 1988.
Homsy et al., Science, 244:1357–1360, 1989.
Miller, Nature—News and Views, 332:109–110, 1988.
Patarroyo et al., Nature 332:158–161, 1988.
Maddon et al., PNAS, 84:9155–9159, 1987.
Sternberg et al., FEBS Letts., 218(2):231–237, 1987.
Nara et al., PNAS, 84:3797–3801, 1987.
Wain–Hobson et al., Cell, 40:9–17, 1985.
Watari et al., J. Exp. Med., 165:459–470, 1987.
Heber–Katz et al., Modern Approaches to Vaccines, Cold Spring Harbour Laboratory, 1985. Abstract.
Heber–Katz et al., Modern Approaches to Vaccines, Cold Spring Harbour Laboratory, p. 63, 1985. Abstract.
Schild et al., Eur. J. Immunol., 21:2649–2654, 1991.
Maddox, J., Nature, 353:297, 1991.
Anderson, C., Nature, 353:287, 1991.
Kion, T. and Hoffman, G., Science, 253:1138–1140, 1991.
Kaneshima et al., Proc. Natl. Acad. Sci. USA, 88:4523–4527, 1991.
Clerici et al., J. Immunol., 146(7):2214–2219, 1991.
Freed et al., J. Virol., 65(1):190–194, 1991.
Freed & Risser, AIDS Res. Human Retroviruses, 7(10):807–811, 1991.
Murakami et al., BBA, 1079:279–284, 1991.
Berzofsky et al., FASEB J., 5:2412–1418, 1991.
Aichele et al., J. Exp. Med., 171:1815:1820, 1990.
Hosmalin et al., PNAS, 87:2344–2348, 1990.
Sastry & Arlinghaus, Hematologic Pathology, 4(3):157–159, 1990.
Takahashi et al., "Induction of Broadly Cross–Reactive Cytotoxic T Cells Recognizing an HIV–1 Envelope Determinant," Science, 255:333–336, 1992. Published in USA.
Rénia et al., "In Vitro Activity of CD4+ and CD8+ T Lymphocytes from Mice Immunized with a Synthetic Malaria Peptide," Proc. Natl. Acad. Sci. USA, 88:7963–7967, 1991. Published in USA.
Hart et al., "Priming of Anti–Human Immunodeficiency Virus (HIV) CD8+ Cytotoxic T Cells In Vivo by Carrier––Free HIV Synthetic Peptides," Proc. Natl. Acad. Sci. USA, 88:9448–9452, 1991. Published in USA.
Gao et al., "Priming of Influenza Virus–Specific Cytotoxic T Lymphocytes Vivo by Short Synthetic Peptides," J. Immunol., 147(10):3268–3273, 1991. Published in USA.
Schulz et al., "Peptide–Induced Antiviral Protection by Cytotoxic T Cells," Proc. Natl. Acad. Sci. USA, 88:991–993, 1991. Published in USA.
Sette et al., "A Microcomputer Program for Hydrophilicity and Amphipathicity Analysis of Protein Antigens," Molec. Immunol., 23(8):807–810. Published in Great Britain.
Coates et al., "AIDS Vaccine Predictions," Nature, 326:549–550, 1987.
Margalit et al., "Prediction of Immunodominant Helper T cell Antigenic Sites from the Primary Sequence," J. Immunol., 138(7):2213–2229, 1987. Published in USA.
DeLisi, C. and J. Berzofsky, "T–cell Antigenic Sites Tend to be Amphipathic Structures," Proc. Natl. Acad. Sci. USA, 82:7048–7052, 1985. Published in USA.
Sastry & Arlinghaus, "Identification of T–Cell Epitopes Without B–Cell Activity in the First and Second Conserved Regions of the HIV Env Protein," Current Science, 5(6):699–707, 1991.
Lasarte et al., "Induction of Cytotoxic T Lymphocytes in Mice Against the Principal Neutralizing Domain of HIV–1 by Immunization with an Engineered T–Cytotoxic–T–Helper Synthetic Peptide Construct," Cellular Immunology, 141:211–218, 1992.
Cohen, "AIDS Research Shifts to Immunity," Science, 257:152–154, 1992.
Sastry et al., "Rapid in Vivo Induction of HIV–Specific CD8+ Cytotoxic T Lymphocytes by a 15–Amino Acid Unmodified Free Peptide from the Immunodominant V3–Loop of GP120," Virology, 188:502–509, 1992.
Berzofsky et al., "Epitopes of HIV and SIV. I. Host Responses," Aids Res. Hum. Retroviruses, 7(2):144, 1991.
Dadaglio et al., "Epitope Recognition of Conserved HIV Envelope Sequences by Human Cytotoxic T Lymphocytes," J. Immunol., 147(7):2302–2309, 1991.
Gao et al., "Priming of Influenza Virus–Specific Cytotoxic T Lymphocytes Vivo by Short Synthetic Peptides," J. Immunol., 147(10):3268–3273, 1991.
Houghten, Richard A., "Synthetic Heat–Stable Enterotoxin Polypeptide of Escherichia coli and Multimers Thereof," Chemical Abstracts, Abstract No. 50888r, 102:323, 1985, regarding WO 84/02,700, Scripps Clinic and Research Foundation.
Kemp et al., "Diagnostic and Antiviral Applications of Synthetic HIV–1 Peptides," In Peptides: Chemistry, Structure and Biology, Proceedings of the Eleventh American Peptide Symposium, Jean E. Rivier and Garland R. Marshall, Eds., Jul. 9–14, 1989, La Jolla, CA.

Kloetzer et al., "Peptides of Feline Leukemia Virus Protein p15 E as Immunosuppressants and Vaccines," *Chemical Abstracts*, Abstract No. 90420x; 111:82, 1989, regarding WO 88/05,783, Ortho Pharmaceutical Corp.

McMichael et al., "Peptide Fragments of Human Immunodeficiency Virus (HIV) for Stimulation of Cytotoxic T–Cell Immunity," *Chemical Abstracts*, Abstract No. 215075v, 112:487, 1990, regarding EP 346,022, Medical Research Counsel.

Shinnick et al., "Synthetic Polypeptides, Antibodies, Diagnostic Systems, and Kits for Immunological Detection of Infections with Tuberculosis Mycobacteria," *Chemical Abstracts*, Abstract No. 36241s, 108:496, 1988, regarding WO 87/01,118, Scripps Clinic and Research Foundation.

Takahashi et al., "A Single Amino Acid Interchange Yields Reciprocal CTL Specificities for HIV–1 gp160," *Science*, 246:118–121, 1989.

Clark, William R., *The Experimental Foundations of Modern Immunology*, John Wiley & Sons, publishers, pp. 278–283, 1980.

Arthos et al., "Identification of the Residues in Human CD4 Critical for the Binding of HIV", Cell, 57:469–481, 1989.

Bates et al., "A predicted three–dimensional structure for the human immunodeficiency virus binding domains of CD4 antigen", Protein Engineering, 3 (1):13–21, 1989.

Capon et al., "Designing CD4 immunoadhesins for AIDS therapy", Nature, 337:525–530, 1989.

Chaudhary et al., "Selective killing of HIV–infected cells by recombinant human CD4–*Peudomonas* exotoxin hybrid protein", Nature, 335:369–372, 1988.

Deen et al., "A soluble form of CD4 (T4) protein inhibits AIDS virus infection", Nature, 331:82–84, 1988.

Finberg et al., "Prevention of HIV–1 Infection and Preservation of CD4 Function by the Binding of CPFs to gp120", Science, 249:287–291, 1990.

Ghetie et al., "CD4 peptide–protein conjugates, but not recombinant human CD4, bind to recombinant gp120 from the human immunodeficiency virus in the presence of serum from AIDS patients", *Proc. Natl. Acad. Sci. USA*, 88:5690–5693, 1991.

Ibegbu et al., "Structural Features of CD4 Required for Binding to HIV", The Journal of Immunology, 142:2250–2256, 1989.

Jameson et al., "Location and Chemical Synthesis of a Binding Site for HIV–1 on the CD4 Protein", Science, 240:1335–1339, 1988.

Lasky et al., "Delineation of a Region of the Human Immunodeficiency Virus Type 1 gp120 Glycoprotein Critical for Interaction with the CD4 Receptor", Cell, 50:975–985, 1987.

Lifson et al., "Synthetic CD4 Peptide Derivatives That Inhibit HIV Infection and Cytopathicity", Science, 241:712–716, 1988.

Marastoni et al., "Synthesis, metabolic stability and chemotactic activity of peptide T and its analogues", *Int. J. Peptide Protein Res.* 35:81–88, 1990.

Till et al., "HIV–Infected Cells Are Killed by rCD4–Ricin A Chain", Science, 242:1166–1168, 1988.

Traunecker et al., "Soluble CD4 molecules neutralize human immunodeficiency virus type 1", Nature, 331:84–86, 1988.

Watanabe et al., "Effects of recombinant soluble CD4 in rhesus monkeys infected with simian immunodeficiency virus of macaques", Nature, 335:267–270, 1989.

Ghiara et al., "Crystal Structure of the Principal Neutralization Site of HIV–1," *Science*, 264:82–85, 1994.

Inhibition of HIV-1 infection of HeLa cells by CD4 Peptide C42

Inhibition of HIV-1 infection of HeLa cells by CD4 Peptide C41

CD4 PEPTIDES FOR BINDING TO VIRAL ENVELOPE PROTEINS

The government owns certain rights in the present invention pursuant to NIH grant AI-29308.

BACKGROUND OF THE INVENTION

The entire text of each of the following disclosures is specifically incorporated herein by reference without disclaimer: Ser. No. 07/945,865, filed Sep. 16, 1992; Ser. No. 07/800,832, filed Dec. 2, 1991; Ser. No. 07/410,727, filed Sep. 20, 1989, now issued as U.S. Pat. No. 5,128,319; and Ser. No. 07/090,646 filed 28 Aug. 1987.

1. Field of the Invention

The present invention relates generally to compositions and methods for binding to and inactivating viruses and for protecting cells from viral infection. More particularly, it concerns compositions and methods for binding to and inactivating HIV gp120 and protecting target CD4$^+$ cells, such as T cells, from infection by HIV. Peptides including short CD4 receptor sequences are identified which are surprisingly effective at interacting with HIV gp120 and in inhibiting or reducing HIV infection of human CD4$^+$ cells. The invention thus encompasses improved CD4-based peptide formulations with gp120 binding functions and HIV-infection inhibitory activity.

2. Description of the Related Art

AIDS was first recognized in the United States in 1981; the number of cases has been increasing at a dramatic pace since then. Several million AIDS infections have now been reported in the United States alone (Rees, 1987). Once significant immunosuppressive symptoms appear in an infected individual, the expected outcome of the infection is death. There is currently no known treatment that can indefinitely delay or prevent the fatal consequences of the disease. Although the disease first manifested itself in homosexual or bisexual males and intravenous drug abusers, it has now spread to others by means such as intimate sexual contact with or receipt of blood products from a carrier of the virus.

The causative agent associated with AIDS has been identified as a group of closely related retroviruses commonly known as Human T Cell Lymphotrophic Virus-type III (HTLV-III), Lymphadenopathy Viruses (LAV), AIDS-Related Viruses (ARV), or more recently named Human Immunodeficiency Virus (HIV). These viruses will be collectively referred to herein for convenience as HIV.

Like other retroviruses, HIV has RNA as its genetic material. When the virus enters the host cell, a viral enzyme known as reverse transcriptase copies the viral RNA into a double stranded DNA. The viral DNA migrates to the nucleus of the cell where it serves as a template for additional copies of viral RNA which can then be assembled into new viral particles. The viral RNA can also serve as messenger RNA (mRNA) for certain viral proteins, including the viral core proteins p18, p24 p13, and reverse transcriptase. RNA may also or be "spliced" into specific viral mRNAs necessary to produce several other viral proteins including two glycosylated structural proteins known as gp41 and gp120 which are inserted in the outer membrane of the virus (Wain-Hobson et al., 1985). Purified gp120 is known to induce antibody in the goat, horse and rhesus monkey that neutralizes HIV in lab tests (Robey et al., 1986).

The primary event in the infection of target cells by HIV is the interaction between the external viral envelope glycoprotein, gp120, and its cellular receptor, CD4 (Lasky et al., 1987). Although the gp120:CD4 interaction is essential for HIV-1 entry into cells, this knowledge has yet to lead to the development of an effective clinical strategy to prevent HIV infection. Certain peptides from gp120 V3 function to inhibit HIV infection (U.S. patent application Ser. No. 07/945,865). However, De Rossi et al. (1991) reported that V3-derived synthetic peptides actually enhanced HIV-1 infection of cells through a CD4-dependent mechanism.

The CD4 molecule has been investigated as a basis for developing anti-HIV strategies. CD4 constructs have been designed with the aim of killing cells already infected with HIV. Such conjugates include CD4 molecules linked to Pseudomonas exotoxin, or Ricin A Chain, which have been reported to selectively kill HIV-infected cells (Chaudhary et al., 1988; Till et al., 1988). CD4 peptide-toxin conjugates have also been shown to be effective at killing HIV-infected cells (PCT Patent Application, WO 91/04050).

The properties of CD4 and CD4-based constructs have also been investigated in regard to inhibiting HIV infectivity. For example, recombinant soluble CD4 molecules (rsCD4) have been shown to neutralize and inhibit AIDS virus infection in vitro (Deen et al., 1988; Traunecker et al., 1988), and to have some beneficial effects in rhesus monkeys infected with simian immunodeficiency virus of macaques (Watanabe et al., 1989). Certain CD4 conjugates have also been constructed, including CD4 "immunoadhesins" in which a CD4 segment is linked to an antibody Fc portion (Capon et al., 1989), and CD4 segments conjugated to ovalbumin (Ghetie et al., 1991). However, such molecules, being relatively large, have many drawbacks which limit any potential therapeutic usefulness.

Smaller molecules, including CPFs (Findberg et al., 1990) and certain CD4-based peptides (Jameson et al., 1988; Arthos et al., 1989), have also been assessed as potential anti-HIV agents. However, this has not lead to the identification of any particularly effective inhibitory compounds. Other non-peptide therapeutic agents, particularly AZT, have recently shown disappointing results in longer-term clinical trials in AIDS patients (Cohen et al., 1993). It is therefore evident that there is currently a great need for improved anti-HIV agents, particularly those capable of inhibiting HIV infection of target cells.

SUMMARY OF THE INVENTION

The present invention addresses one or more of the foregoing or other disadvantages in the prior art by providing improved peptide compositions, one use of which is in methods to inhibit HIV infection. The peptide compositions and therapeutic formulations of the invention generally comprise synthetic peptides including short CD4 sequences which have been found to be surprisingly effective at interacting with HIV gp120 and also, for example, in protecting human CD4$^+$ cells, such as T cells, from HIV infection.

This invention particularly concerns improved peptide compositions, and formulations thereof, which include one or more viral binding peptides as disclosed herein. As used herein, the terms "viral binding peptide" and "viral inactivating peptide" are used interchangeably to refer to relatively small peptides which include within their sequence a short sequence derived from the CD4 molecule, which peptides are capable of binding to a virus envelope protein, most particularly, to gp120, and are capable of inactivating virus. These viral binding and inactivating functions confer various useful properties to the peptides of the invention. For example, they may be used to inactivate viruses, particularly HIV, within blood and body fluid samples, and they may even be used in assays to identify HIV virus and HIV-infected cells, which are known to express gp120.

The viral binding and inactivating properties of the class of small CD4-derived peptides presently disclosed also renders them capable of inhibiting viral infection of target cells. Indeed, such peptides are herein shown to function particularly well in inhibiting HIV infection of $CD4^+$ cells, such as $CD4^+$ T Cells. As such, the peptides of the invention may also be referred to as "viral binding inhibition peptides". This term is used to indicate that the peptides can, by means of their own virus inactivating functions, prevent viruses from binding to other structures, particularly receptors present on target cells. Thus, the viral binding inhibition peptides and therapeutic formulations thereof may be employed in methods to reduce or inhibit viral infection, and particularly, to inhibit HIV infection of $CD4^+$ cells.

Peptides of the present invention may also be characterized as 4 to 10 or so residue CD4-derived peptides, or di-arginine peptides. These classes of peptides are each capable of binding to gp120 and, also, of inhibiting the HIV infection process by steric hinderance or catalytic inactivation of gp120. In preferred embodiments, the invention is directed to a composition comprising a viral inactivating or viral binding inhibition peptide of from 4 to about 10 amino acids in length including within its sequence the amino acid sequence Ser Arg Arg Ser (seq id no:1), in accordance with amino acids 57–60 of CD4, the peptide being capable of binding to HIV gp120.

Peptides of from 4 to about 8 or about 6 residues which include the Ser Arg Arg Ser (seq id no:1) sequence are preferred, with the tetrapeptide consisting of the amino acid sequence Ser Arg Arg Ser (seq id no:1) itself being most preferred. Where longer peptides are employed, the most preferred are contemplated to be those peptides in which the residues in addition to Ser Arg Arg Ser are also derived from the surrounding sequence in the CD4 molecule. In certain other preferred embodiments, the invention is also directed to a composition comprising a viral binding or inactivating arginine-arginine (Arg Arg) dipeptide, the dipeptide being capable of binding to HIV gp120.

The use of the C41 peptide is particularly advantageous as the inventors surprisingly found this peptide to have HIV inhibitory activity equivalent to that of a 22 residue long peptide (FIG. 2). The use of shorter peptides such as dipeptides or peptides of about 4 to 10 residues in length is preferred over the longer peptides in the prior art, as exemplified by Jameson et al. (1988) and Arthos et al. (1989), as short peptides are easy to prepare, cost-effective, less immunogenic and have longer bioavailability. A further important advantage of the class of small peptides disclosed herein is that their viral binding and inhibitory capacities are believed to function independently of the presence of anti-gp120 antibodies, such as those inhibitory antibodies present within HIV patients' sera.

Where peptides longer than 2 or 4 amino acids are employed, it is contemplated that they may include virtually any other amino acid sequence (in addition to the Arg Arg or Ser Arg Arg Ser sequences) so long as the resultant peptide maintains its viral binding, i.e., gp120 binding, capacity. However, as mentioned above, in preferred embodiments, the use of peptides including longer sequences from the CD4 molecule is contemplated. The present invention thus encompasses peptides including the sequence Ala Asp Ser Arg Arg Ser (seq id no:2) corresponding to amino acids 55–60 of CD4; peptides including the sequence Asp Arg Ala Asp Ser Arg Arg Ser (seq id no:3) corresponding to amino acids 53–60 of CD4; and also peptides having the sequence Leu Asn Asp Arg Ala Asp Ser Arg Arg Ser (seq id no:4) corresponding to residues 51–60 of CD4. It will also be understood that peptides capable of binding gp120 which include the Ser Arg Arg Ser sequence along with other sequences from within CD4, for example, along with the sequences of amino acids 61 upwards, such as 61–65 or so, also fall within the scope of the invention.

The present invention also encompasses therapeutic formulations, including those for parenteral administration, comprising one or more of the above-described peptides dispersed in a pharmacologically acceptable vehicle. As the peptides are derived from CD4 and the CD4:gp120 interaction is essential to HIV infectivity, such peptides are envisioned to be particularly useful in inhibiting cellular infection by a variety of different HIV isolates and strains. However, as will be generally understood by those of skill in the art, such inhibitory formulations are designed for use in treatment, such as to reduce infection, and are not suggested to be a "cure" for AIDS.

Synthetic peptides may be modified for use in therapeutics, for example, by employing one or more d-amino acids in place of l-amino acids, by adding groups to the N- or C-termini, such as by acylation or amination, or by encapsulating the peptides within liposomes. The peptides could also be incorporated in a biocompatible coating designed for slow-release. The preparation and use of appropriate therapeutic formulations will be known to those of skill in the art in light of the present disclosure. The peptides of the present invention may also be used as part of a prophylactic regimen designed to prevent, or protect against, possible HIV infection. In this sense, in addition to pharmacological formulations similar to those for therapeutics, one or more of the above-described peptides may also be formulated into a creme, lotion or douche.

In further embodiments, the invention concerns methods for binding HIV gp120 which generally comprise contacting HIV gp120 with a composition comprising a viral binding peptide, dipeptide or composition in accordance with those disclosed herein. These methods are suitable for binding HIV gp120 in the form of isolated gp120 proteins or gp120 peptides which have the CD4 binding regions located within their structure. The methods are also applicable to binding gp120 within HIV virus particles and virions, HIV-infected cells or, indeed, any other composition containing HIV gp120. Most often, binding will be accompanied by inactivation of gp120.

The gp120 binding and inactivating properties of the peptides lend themselves to methods for use in inhibiting the binding of HIV to target cells and, thereby, to methods for use in inhibiting HIV infection of $CD4^+$ target cells, such as T cells. To inhibit HIV binding to, or infection of, a $CD4^+$ cell in accordance herewith, one would contact the HIV virus, or a composition containing the HIV virus, with an amount of a viral binding peptide, dipeptide or composition effective to inactivate the virus and thereby inhibit HIV binding and infection. These inhibitory methods may be used in connection with various functional embodiments, both in vitro, as part of laboratory techniques, and in vivo, for example, in connection with clinical treatment embodiments.

Clinical methods for inactivating HIV and inhibiting HIV binding to, and infection of, target cells within the body of an animal, including a human subject, constitute one aspect of this invention. Such methods generally comprise contacting HIV, or a composition containing HIV viral particles, with an immunologically effective amount of a viral binding and inactivating peptide, dipeptide or composition in accordance with those described herein. As used herein, an "immunologically effective amount" refers to an amount of a viral binding peptide or composition sufficient to bind to and inactivate gp120 such that HIV binding to, and infection of, target $CD^+$ cells is significantly inhibited or reduced. In these clinical embodiments, the HIV virions and virus particles would be contacted in vivo by administering the peptide or composition to an animal, such as a human subject, known or suspected to be infected with HIV.

The viral binding and inactivating peptides of the present invention will also have utility in embodiments other than in clinical treatment and may be employed in a variety of in vitro assay protocols in addition to protecting cultured cells from HIV infection. For example, peptides, particularly those longer than about 6 amino acids, may also be used as immunogens to generate anti-CD4 peptide antibodies which have many uses, such as, e.g., in HIV-binding assays, in CD4 binding assays to identify CD4 positive cells in biological samples, or to probe the structure:function relationships of CD4. Also, as the CD4-derived peptides of the invention bind to gp120, it is conceivable that they may be employed in assays to identify the HIV virus itself or HIV-infected cells which are known to express gp120. Such assays could utilize radioactively- or enzymatically-labelled peptides or anti-peptide antibodies such as those described above.

The invention also provides methods for inactivating a virus, particularly HIV, located within a sample, thereby rendering the sample free from active, infectious virus. Such methods comprise, generally, contacting a sample suspected of containing HIV with a composition comprising a peptide or dipeptide in accordance with those described herein under conditions effective to allow binding of the peptide to gp120-expressing HIV which may be present within the sample. Under the chosen conditions, the peptide and the gp120 portion of HIV would then form a complex, and the peptide would act to inactivate HIV, thus removing functional HIV from the sample.

Preferred methods for using the peptides of the invention to inactivate HIV within, for example, blood or other body fluid samples, involve first attaching or immobilizing the peptide to a solid support. Solid supported peptides therefore form another aspect of the invention and may be prepared in the form of a column, i.e., an HIV gp120 affinity column, resin, filter or other solid medium, so long as the peptide is available to hybridize with HIV gp120. This may be achieved using one or more of the many attachment methods known to those of skill in the art, as exemplified by creating sterile agarose or sepharose columns or other HPLC resins with appended peptide groups. Such supports and columns may then be used, for example, as disposable columns and filters for cleansing blood and blood by-products. The blood products would be passed over the column or solid support to ensure that no functional HIV remains present within the sample.

Another example of a potential use for the viral binding and inactivating peptides concerns their use in methods for detecting the presence of HIV gp120 within a sample suspected of containing HIV gp120, HIV virus particles or HIV-infected cells. These methods include contacting the sample suspected of containing HIV gp120 with a peptide or composition in accordance with the present invention under conditions effective to allow the active peptide or peptides of the composition to form a complex with gp120 from the sample. One would then detect the presence of the complex by detecting the presence of the peptide(s) within the complex, e.g., by originally using radiolabelled peptides or by subsequently employing anti-peptide antibodies and standard secondary antibody detection techniques.

In addition to the positive HIV-related effects proposed to occur through a gp120 deactivation mechanism, it is also envisioned that this disulfide bond cleavage induced by di-arginine may be a more common means of inducing conformational changes in proteins. Accordingly, further uses for the peptides and dipeptides of the present invention are contemplated to include the specific in vitro reduction of disulfide bonds, e.g., to deactivate an enzyme or receptor; or to probe for pathophysiological changes in order to facilitate more accurate diagnoses.

BRIEF DESCRIPTION OF THE DRAWINGS

FIG. 2A. Inhibition of HIV-1 infection of HeLa cells by the 22 residue CD4-peptide termed C42 (CD4 region 39–60; seq id no:5). Various concentrations of peptide C42, ranging between 250 ug/ml to 0.001 ug/ml, were pre-mixed with infectious virus. After 30 minutes incubation at 37° C., the peptide-virus mixture was added to the monolayer of Hela cells in a petridish and incubated for 7 days at 37° C. At the end of the incubation period the culture medium was analyzed for reverse transcriptase (RT) activity as a measure of virus production. As a negative control an unrelated peptide from the c-mos proto-oncogene was used. Other controls included cells incubated with medium alone or with virus that was not pre-incubated with the test peptide. RT inhibition with c-mos peptide was about 15–20%.

FIG. 2B. Inhibition of HIV-1 infection of HeLa cells by the 4 residue CD4-peptide termed C41 (CD4 region 57–60; seq id no:1). These studies were conducted as described above for FIG. 2A except that peptide C41 was employed rather than C42.

DETAILED DESCRIPTION OF THE PREFERRED EMBODIMENTS

Figure 1:
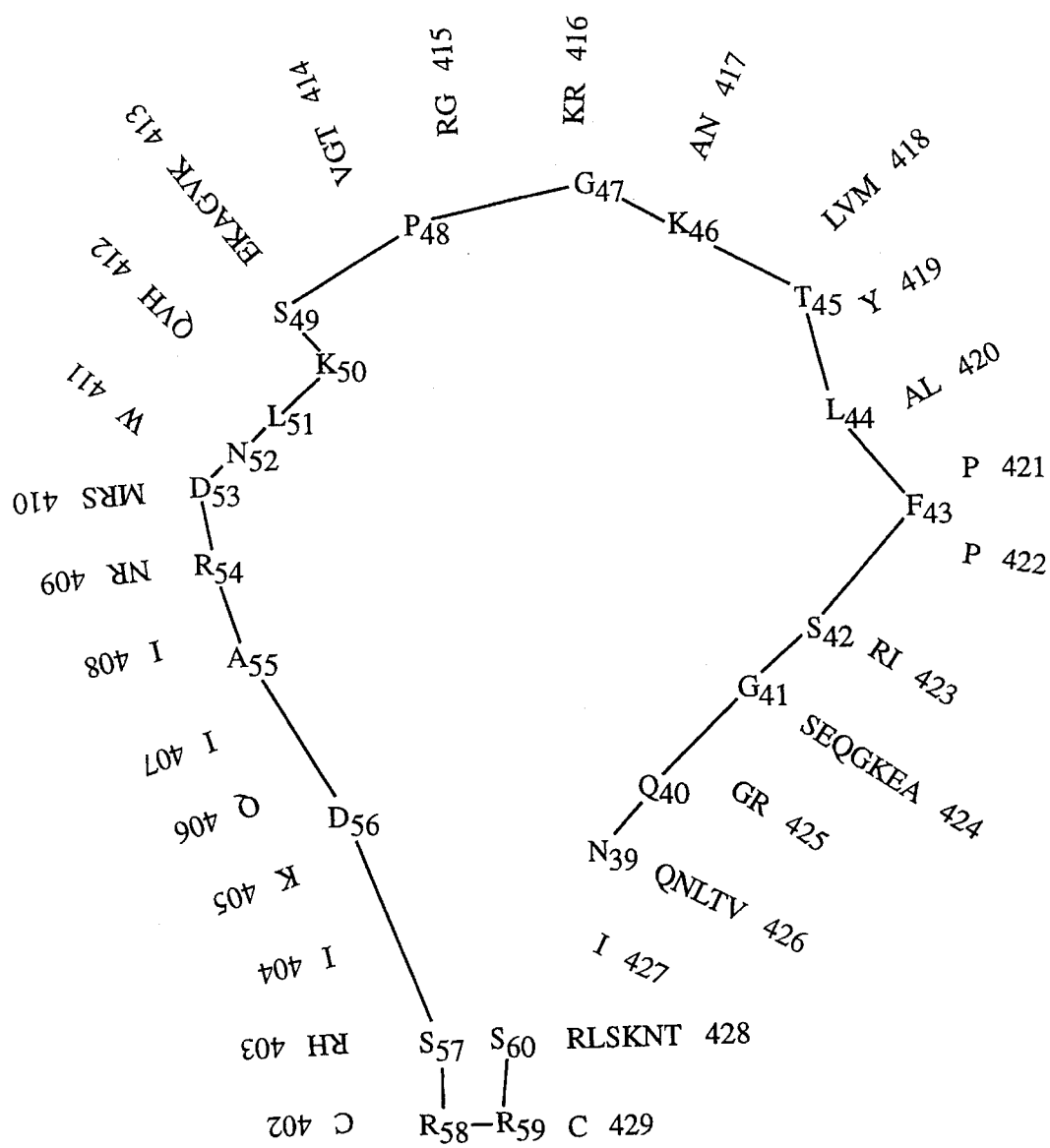
FIG. 1. Two dimensional illustration of the gp120-CD4 interaction. The outer ring is a composite of HIV gp120 high affinity CD4 binding regions, contained within amino acids 402–429, which are known to be present within different HIV isolates. The various possible amino acids at each location are represented in the one letter amino acid code. Therefore, the amino acids shown are not peptides but represent various distinct amino acids which have been found within HIV gp120. These variations are mapped onto the high affinity CD4 binding region 40–60 on the inner connected ring.

AIDS is a highly infectious and fatal disease caused by a group of closely related retroviruses commonly known as HIV. There are currently no vaccines to prevent HIV infection and no effective therapeutic agents to arrest progression once infection has been initiated. The present invention addresses these current failings through the use of peptide technology in the development of CD4-based anti-viral therapeutics.

HIV-target cell interactions involve the viral molecule gp120 and the cell surface molecule CD4. The V3 loop region of gp120 is known to be essential for HIV-1 infection of cells (Travis et al., 1991; Freed and Riser, 1987; Freed et al., 1991). Anti-V3 loop antibodies have been shown to inhibit HIV-1 cellular infection without interfering with gp120 binding to CD4 (Linsley et al., 1988; Javaherian et al. 1989). The V3 loop region is also known to be a target for a trypsin related protease on the host cell surface (Murakami et al., 1991). It has been speculated that after gp120 binds to CD4, the V3 loop is cleaved by a cell surface protease leading to a conformational change in the gp120/gp41 protein complex (McCune et al., 1988). Such a change may then expose the fusogenic domain in the transmembrane protein gp41, resulting in the fusion of the viral particle membrane with the cell membrane.

Anti-HIV strategies have been developed around gp120 peptides, despite early conflicting results in this area. Koito et al. (1989) reported that a synthetic peptide corresponding to the major HIV-1 neutralizing epitope from the V3 loop of gp120 inhibits syncytium formation between the HIV-1 infected CCRF-CEM and uninfected Molt-4 cells in a dose-dependent manner. In these studies a 36 amino acid peptide of residues 303–338 representing the entire V3 loop, was found to inhibit syncytium formation by 30–60% at a concentration of 100 µM (approximately 300 µg/ml). However, a 24 amino acid peptide of residues 308–331 representing the middle portion of the V3 loop was less efficient and was required at 300 µM concentration (approximately 720 µg/ml) to achieve the same level of inhibition of syncytium formation. Neither of these peptides were tested for their capacity to inhibit HIV infection of cells.

In contrast, De Rossi et al. (1991) reported that synthetic peptides of 24 amino acids in length from V3 loop regions of different HIV-1 isolates actually enhance HIV-1 infection of cells through a CD4-dependent mechanism. In these experiments, synthetic peptides at concentrations ranging between 0.62–20 µM (approximately 1.5 to 48 µg/ml) were employed and one human T cell line (Molt-3) was tested.

Studies of the present inventors have recently show that V3 loop synthetic peptides inhibit HIV infection. Synthetic peptides of varying length (8–24 amino acids) selected from the V3 loop of gp120 were determined to be effective at inhibiting HIV infection of T cells, using both cultured human T cells such as H9, CEM and MT-4, and freshly prepared primary human T cells. These peptides include R15K, N24G, D23, D24, D25, D26, D30, D35, D38, D39 and D40, as disclosed in U.S. Ser. No. 07/945,865, filed Sep. 16, 1992, specifically incorporated herein by reference.

Anti-HIV strategies have also been proposed using the CD4 molecule. CD4-based toxin constructs have been reported to kill cells already infected with the HIV virus (Chaudhary et al., 1988; Till et al., 1988; PCT Patent Application, WO 91/04050), and CD4-derived molecules have been reported to inhibit HIV cellular infection (Deen et al., 1988; Traunecker et al., 1988; Ibegbu et al., 1989; Watanabe et al., 1989). However, the CD4 molecules and constructs in these studies are relatively large and have all the associated drawbacks which limit potential therapeutic applications, such as being immunogenic and susceptible to proteolysis.

The gp120 binding site of CD4 has been reported to lie within the first two domains. Studies using truncated and mutant CD4s have indicated the site to lie solely within CD4-I, i.e., residues 1–106, (Arthos et al., 1989). However, mutations to CD4-II have also been shown to reduce the affinity of gp120 binding, possibly due to indirect effects of these CD4-II changes on CD4-I. In one study directed to smaller portions of CD4, Ibegbu et al. (1989) reported that CD4 portions employed to inhibit HIV binding to CD4$^+$ cells should be formulated with a proper tertiary structure, such as the 23 kD proteolytic fragment shown to have inhibitory activity in their study.

Bates et al. (1989) have published a predicted three-dimensional structure for the HIV binding domains of CD4, but despite intensive efforts in this area, there remains confusion as to the precise regions which could have potential for use as inhibitory peptides. For example, Jameson et al. (1988) report that the CD4 regions 32–47, 25–58 and 37–53 constitute the virus binding site; Arthos et al. (1989) report that the region 41–55 is most important; and Vitetta & Uhr (WO 91/04050) use the peptide region 41–57. Moreover, Lifson et al. (1988) have published studies showing that benzyl groups must be attached to CD4 peptides for the peptide to be active. It is therefore apparent that, rather than leading to the identification of more effective compounds, the studies of potentially inhibitory CD4 peptides have generated an amount of contradictory and confusing data.

Following a detailed mechanistic analysis of the likely gp120-CD4 interactions, the present inventors identified candidate viral binding and inactivating peptide sequences contemplated to inhibit or reduce the entry of HIV into human target CD$^+$ cells, including T cells. The peptides are proposed to act either by competitive inhibition, i.e., by steric hinderance, or by catalytic inactivation of CD4-binding epitopes on gp120. In any event, regardless of the mechanism of action, studies showed that the peptides termed C41 (CD4 region 57–60; seq id no:1) and C42 (CD4 region 39–60; seq id no:5) were indeed particularly effective at viral binding and at inhibiting HIV infection of CD4 positive cells.

Other useful peptides contemplated by the inventors include the arginine dipeptide (Arg Arg) and also peptides incorporating longer sequences, and most preferably where those sequences are also derived from CD4. Such peptides include, for example, peptides comprising the sequences Ala Asp Ser Arg Arg Ser (seq id no:2) corresponding to amino acids 55–60 of CD4, or Asp Arg Ala Asp Ser Arg Arg Ser (seq id no:3) from the 53–60 amino acid region of CD4, and also the peptide having the sequence Leu Asn Asp Arg Ala Asp Ser Arg Arg Ser (seq id no:4) corresponding to residues 51–60 of CD4. Where these longer peptides are employed, it will be understood that their biologically functional equivalents also fall within the scope of the present invention.

As used herein, biological functional equivalents are defined as those peptides which include the substitution of arginines with the other positively charged amino acids, lysine and histidine, with lysine being most preferred. Biological functional equivalents also include peptides in which any residue other than arginine, i.e., those at the more terminal positions, has been substituted with any equivalent amino acid. Amino acids at the terminal positions are believed to serve as guides for disulfide destruction and other physiological processes. Any biologically functional equivalent amino acid may be included in these positions, as defined by amino acids whose hydrophilic or hydropathic indices are within ±2, more preferably, within ±1, and most preferably, within ±0.5. Peptides with N-terminal alkylations and C-terminal esterifications are also encompassed within the present invention.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference). The amino acid hydropathic index values are: isoleucine (+4.5); valine (+4.2); leucine (+3.8); phenylalanine (+2.8); cysteine/cystine (+2.5); methionine (+1.9); alanine (+1.8); glycine (−0.4 ); threonine (−0.7 ); serine (−0.8 ); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

Substitution of like amino acids can therefore be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the peptidyl compounds described herein, the inventors also contemplate that other sterically similar compounds may be formulated to mimic the key portions of the peptide structure and that such compounds may also be used in the same manner as the peptides of the invention. This may be achieved by the techniques of modelling and chemical design known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

This invention is particularly concerned with smaller inactivatory and inhibitory peptides such as dipeptides or peptides of about 4–10 or so residues in length, as exemplified by the tetrapeptide C41 (seq id no:1), which are contemplated for use in anti-HIV therapeutics to prevent or reduce viral spread and disease progression in HIV-infected patients. The use of smaller peptides in therapeutics is preferred for various reasons. These include the low cost and ease of large scale preparation, and the reliability of the product. Also their biological properties are preferable, such as the ease with which peptides can penetrate tissues, their low immunogenicity, the fact that they present a smaller target for proteases thus affording longer bioavailability and, further, it is contemplated that they will function effectively even in the presence of anti-gp120 inhibitory antibodies which are known to be present within HIV patients' sera.

Stability examinations which may be performed on the peptides include, for example, pre-incubation in human serum and plasma; treatment with various proteases; and also temperature-and pH-stability analyses. If found to be necessary, the stability of the synthetic peptides may be enhanced by any one of a variety of methods such as, for example, employing d-amino acids in place of l-amino acids for peptide synthesis; using blocking groups like t-boc and the like; or encapsulating the peptides within liposomes. The bio-availability of select mixtures of peptides may also be determined by injecting radio-labelled peptides into mice and rhesus monkeys and subsequently analyzing their tissue distribution.

If stability enhancement was desired, it is contemplated that the use of dextrorotary amino acids (d-amino acids) would be advantageous as this would result in even longer bioavailability due to the inability of proteases to attack these types of structures. The peptides of the present invention may also be further stabilized, for example, by the addition of groups to the N- or C-termini, such as by acylation or amination. If desired, the peptides could also be in the form of lipid-tailed peptides, formulated into surfactant-like micelles, or other peptide multimers. The preparation of peptide multimers and surfactantlike micelles is described in detail in U.S. Ser. No. 07/945,865, incorporated herein by reference.

The small synthetic peptides of the invention are ultimately contemplated for use in anti-HIV therapeutic formulations designed to protect human cells from HIV-1 infection. As the peptides are derived from CD4, the molecular target for HIV infection, they are envisioned to be useful in inhibiting the infection of a variety of different HIV isolates and strains. Furthermore, since such formulations will be completely synthetic and defined, these reagents are contemplated to be particularly advantageous for use in economical and safe anti-HIV therapeutics.

Specific therapeutic formulations may be tested in experimental animal models, such as mice, rats, rabbits, guinea pigs, goats, Rhesus monkeys, chimpanzees, and the like, in order to determine more precisely the dosage forms required. More particularly, they may be tested in higher mammals, such as monkeys and chimpanzees, and in the rabbit model of AIDS disclosed in U.S. Pat. No. 5,183,949, incorporated herein by reference, which models are recognized as the most useful in the art. However, in searching for new treatments for AIDS, it is known that finding a single "cure" is unlikely. Accordingly, treatments which prolong survival, improve health, delay the onset of symptoms and/or slow disease progression are known to represent useful treatments.

Therapeutic or pharmacological compositions of the present invention will generally comprise an effective amount of a small CD4-derived viral binding and inactivating peptide or peptides, dissolved or dispersed in a pharmaceutically acceptable medium. The phrase "pharmaceutically acceptable" refers to molecular entities and compositions that do not produce an allergic, toxic, or otherwise adverse reaction when administered to a human. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated.

Supplementary active ingredients can also be incorporated into the therapeutic compositions of the present invention. For example, the viral binding peptides may also be combined with peptides including cytotoxic T cell- or T helper cell-inducing epitopes (as disclosed in U.S. Ser. No. 07/945,865) to create peptide cocktails for immunization and treatment. Alternatively, compounds with other known or proposed anti-viral activities may also be added if desired.

The preparation of pharmaceutical or pharmacological compositions containing viral binding peptide or peptides, including dextrorotatory peptides, as an active ingredients will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalents and the like.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile solutions suitable for intravenous administration are preferred in certain embodiments and are contemplated to be particularly effective in reducing virus load and slowing down the onset of immunodeficiency. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A peptide or peptides can be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

The preparation of more, or highly, concentrated solutions for intramuscular injection is also contemplated. This is envisioned to have particular utility in facilitating the treatment of needle stick injuries of health care workers. In this regard, the use of DMSO as solvent is preferred as this will result in extremely rapid penetration, delivering high concentrations of the active peptide, peptides or agents to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, including the peptides alone, or in conjunction with antifungal reagents. Inhalant forms are also envisioned, which again, may contain active peptides or agents alone, or in conjunction with other agents, such as, e.g., pentamidine. The therapeutic formulations of the invention may also be prepared in forms suitable for topical administration, such as in cremes and lotions.

Buffered ophthalmic solutions also fall within the scope of the invention. These may be used in connection with patients suffering from HIV-associated retinitis. The buffering is necessary due to pH changes the peptide may cause. Ophthalmic preparations may be created in accordance with conventional pharmaceutical practice, see for example "Remington's Pharmaceutical Sciences" 15th Edition, pages 1488 to 1501 (Mack Publishing Co., Easton, Pa.).

Suitable ophthalmic preparations will generally contain a novel dipeptide, peptide or agent as disclosed herein in a concentration from about 0.01 to about 1% by weight, and preferably from about 0.05 to about 0.5%, in a pharmaceutically acceptable solution, suspension or ointment. The ophthalmic preparation will preferably be in the form of a sterile buffered solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed. As used herein, "pharmacologically effective amount" means an amount of composition is used that contains an amount of a CD4-derived viral binding peptide or peptides sufficient to significantly inhibit or prevent HIV infection of cells in the host animal (mammal).

In this context, the quantity of peptide(s) and volume of composition to be administered depends on the host animal to be treated, such as, the capacity of the host animal's immune system to fight HIV infection. Precise amounts of active peptide required to be administered depend on the judgment of the practitioner and are peculiar to each individual. However, the peptides are shown to be particularly effective in vitro with one nanogram/ml giving 40% inhibition. Suitable dosage ranges for use in humans are therefore contemplated to be those which result in similar local concentrations of peptides. Doses in the order of about 1 μg/kg/day to about 500 μg/kg/day, preferably about 10 μg/kg/day to about 200 μg/kg/day, and more preferably about 50 μg/kg/day of active ingredient peptide per individual are contemplated.

A minimal volume of a composition required to disperse the peptide is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Oral formulations may include compounds in combination with an inert diluent or an assimilable edible carrier; those enclosed in hard or soft shell gelatin capsules; those compressed into tablets; or those incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should generally contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

Tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

As the peptides in accordance with the present invention have HIV chemopreventative properties, they could also be utilized as part of a prophylactic regimen designed to prevent, or protect against, possible HIV infection upon sexual contact with an infected individual. In this sense, in addition to those pharmacological formulations described above, one or more peptides or dipeptides may also be formulated into a creme, lotion, douche or into the lining of a condom. The preparation of cremes, lotions and douches containing HIV chemopreventative peptides or agents will also be generally known to those of skill in the art.

Chemopreventative vaginal douche and cremes containing the peptides of the invention may be of use in connection with presexual exposure protection. Such douches and cremes may be formulated in a standard acetic acid solution. The cremes may also be mixed with 9-nonoxynol spermicide to use in conjunction with birth control, or added to condoms. Vaginal sponges containing the peptides form another aspect of the invention, in such cases, the active peptides or agents may be time-released over several hours with nonoxynol.

The peptides may also be formulated in suppository forms for use in connection with chemoprevention during anal sex, because the rectum and large intestine are major sites of HIV infection. In the prevention of oral sex contraction of HIV, the mixing of peptides in slippery oils that taste good (i.e. Motion Lotion or Blow Hot Oil) is also contemplated.

The peptides may be used in their chemopreventative capacity be administering in an amount that is effective in a preventative manner. In this sense, an "effective preventative amount" means an amount of composition that contains an amount of a CD4-derived peptide or peptides sufficient to significantly inhibit or prevent HIV infection of cells in an uninfected animal on contact with an infected animal. If required, for example, by insurance companies, the peptides may also be added to gloves used by health care workers or researchers dealing heavily with blood and bodily fluids or to liquid soap used in hospitals and research institutions.

A further and important use of the peptides described herein concerns their attachment to solid supports and columns, such as sepharose and agarose columns, sterile HPLC resins, and the like. Such supports and columns with appended peptides, e.g., HIV gp120 affinity columns, may be used for inactivating HIV from within blood and other body fluid samples. One particular use would then be as disposable filters for deactivating HIV within blood and blood by-products.

In addition to the positive HIV-related effects proposed to occur through a gp120 deactivation mechanism, it is also proposed that this disulfide bond cleavage induced by diarginine may be a more common means of inducing conformational changes in proteins. Accordingly, further uses for the peptides and dipeptides of the present invention are contemplated to include the specific in vitro reduction of disulfide bonds, e.g., to deactivate an enzyme or receptor; or to probe for pathophysiological changes in order to facilitate more accurate diagnoses.

The following examples are included to demonstrate preferred embodiments of the invention. It will be appreciated by those of skill in the art that the techniques disclosed in the examples which follow represent techniques discovered by the inventors to function well in the practice of the invention, and thus can be considered to constitute preferred modes for its practice. However, those of skill in the art will, in light of the present disclosure, appreciate that many changes can be made in the specific embodiments which are disclosed and still obtain a like or similar result without departing from the spirit and scope of the invention.

EXAMPLE 1

Preparation of Peptides, Peptide Polymers and Peptide Micelles

Synthetic peptides of 4 to about 10 or 11 or so amino acid residues in length corresponding to the CD4 sequences can be readily prepared using the solid-phase technique of Merrifield (1963) using a modified Vega 250 automated peptide synthesizer or by the "bag" method described in Houghten (1985). In either case, removal of the t-butyloxycarbonyl (t-BOC) amino acid blocking groups and the hydrolysis of the peptide from the resin can be carried accomplished by hydrofluoric acid (HF) treatment at 0° C. for one hour. The peptide-containing mixture can then be extracted with diethyl ether to remove non-peptide organic compounds and the synthesized peptides extracted from the resin with 25% acetic acid (w/v).

Two types of multimeric forms of the peptides can also be prepared if desired, according to the following methodology. Di-cysteine (di-Cys terminated) polymers in which a plurality of peptides are linked end-to-end by disulfide bonds can be prepared. These di-cysteine polymers are produced by adding cysteine residues to the termini of each peptide during synthesis. The di-cysteine-terminated (di-Cys) peptides are then dissolved (10 mg/ml) in ammonium bicarbonate (0. Lm) at room temperature (~25° C.) and stirred for about 16 hours to effect oxidation of the sulfhydryl groups to produce polymer forms of the peptides. The peptide solution can be freeze-dried and analyzed by HPLC to confirm the presence of polymer forms of the peptide.

Surfactant-like micelles can also be formed by linkage of an amino-terminal lysine-containing spacer peptide (Lys-Gly-Gly-) to the peptide sequence to form a composite polypeptide, and then coupling a $C_{12}$–$C_{18}$ fatty acid, such as palmitic acid, to both the alpha and epsilon amino groups, as in Hopp (1984). The $C_{12}$–$C_{18}$ fatty acid-containing peptides produced can then be extracted in 95% acetic acid and utilized to form large micelles in the aqueous composition that exhibit increased immunogenicity relative to the peptides.

EXAMPLE 2

Anti-Peptide Antibody Response

Aqueous compositions of the peptides and peptide multimers can be assayed for their ability, or lack of ability, to elicit an anti-peptide antibody response in BALB/c mice, an immunocompetent mouse strain, as described below.

Groups of BALB/C mice (6–8-week-old females, 3 to 5 mice/group, Charles River Laboratories) would be immunized by subcutaneous (s.c.) or intraperitoneal (i.p.) injection of a peptide multimer (100 μg/injection) in complete Freund's adjuvant (CFA) (1:1 ratio). Booster injections (50 μg of peptide multimer) in incomplete Freund's adjuvant (IFA) (1:1) would be given at 6 and 10 weeks after the initial immunization. Each mouse would be bled from its retro-orbital plexus at two-week intervals and the serum pooled for individual mice in each group.

An ELISA assay would then be performed on each serum to detect the presence of anti-peptide antibodies, e.g., utilizing peroxidase-conjugated goat anti-mouse IgG (Boehringer Mannheim Biochemicals, Indianapolis, Ind.) as the second antibody.

EXAMPLE 3

T Cell Responses

Peptides and polymeric forms of the peptides may be assayed for their elicitation of a T cell proliferative response as described in Milich et al. (1985) and below.

Mice (3 or 5 mice/group of, e.g., B6C3 F1 mice, $H-2^{kxb}$, Charles River Laboratories and A.SWXBALB/C F1 mice, $H-2^{sxd}$, Jackson Labs, Bar Harbor, Me.) would be injected in the right hind footpad with a 1:1 mixture of peptide polymer (100 μg/injection) and CFA. Draining popliteal lymph node (PLN) cells would then be harvested after ten (10) days, and cultured ($2 \times 10^5$ cells/well), e.g., in 96-well microtiter plates in 0.2 ml of Click's medium (Click et al., 1972) containing various concentrations of synthetic peptide, gp160, an unrelated proteinaceous material or medium alone, for 96 hours at 37° C. in a humidified atmosphere of 5% $CO_2$. During the final 16–18 hours of culturing, $^3H$-thymidine ($^3H$-TdR) (1 μCi/well, 6–7 Ci/mmole, ICN Radiochemicals) should be added. The cells should then be harvested onto filter strips to allow $^3H$-TdR incorporation to be monitored.

Results from such studies can be expressed as a stimulation index (SI) representing the fold increase in radioactivity counts in the presence of antigen compared to background values where no antigen was added. Non-specific proliferation of PLN cells can be determined by including an unrelated peptide in the assays.

EXAMPLE 4

Induction of HIV-Specific Cytotoxic T Lymphocytes

Groups of 3 to 5 syngeneic female mice (6 to 8 weeks of age) may be immunized by intradermal injection in an appropriate site with an aqueous composition containing an immunizing (CTL-stimulating) amount of peptide either as monomer or as the before-discussed multimers in CFA (1:1). Ten (10) days after immunization, draining PLN cells and spleen lymphocytes should be obtained and restimulated in vitro by culturing for six (6) days with irradiated syngeneic normal spleen cells that were pre-treated with the same synthetic peptide as immunogen.

The presence of cytotoxic T lymphocytes (CTL) is determined by a 4-hour $^{51}Cr$ release assay as follows. The PLN cells are maintained for five days at 37° C. in Clicks medium containing 10% fetal calf serum (FCS) together with irradiated syngeneic normal spleen cells that were pre-treated with the appropriate test peptide. These cells are designated as the effector cells, and express $H-2^d$ MHC class I antigen.

Target cells (phytohemagglutinin-stimulated (PHA) blasts of syngeneic mouse spleen cells or P815 mouse cells expressing a corresponding HIV protein) are washed three times with serum-free RPMI 1640 medium and then admixed, contacted and maintained (incubated) at 37° C. for about 1.5 to about 2 hours together with 250 μCi of sodium chromate (specific activity 200–400 Ci/g of $^{51}Cr$, New England Nuclear, Boston, Mass.). The target cells are subsequently washed with RPMI 1640 medium containing 10%

FCS, and resuspended in RPMI 1640 with 10% FCS and different concentrations of peptide. These cells are then washed 3 times with RPMI containing 10% FCS and resuspended at $5\times10^4$ cells/ml. A 100 µl aliquot of each cell suspension is added to a well of a 96-well-U-bottom microtiter plate.

A 100 µl aliquot of the appropriate effector cell suspension ($5\times10^6$ cells/ml) is added to each well and a twofold serial dilution made to obtain different effector-to-target cell (E:T) ratios. Control wells receive 0.1 ml of RPMI medium with 10% FCS alone in the absence of effector cells to obtain a value for spontaneous $^{51}$Cr release, and receive 0.1 ml of 5% Triton X-100 detergent to obtain a value for maximum $^{51}$Cr release.

The plates are incubated at 37° C. for about 4 hours, following which 100 µl of supernatant from each well is monitored in a gamma counter to determine $^{51}$Cr release. The percent cytotoxicity is calculated as:

$$\frac{\text{(Effector Cell} - \text{Stimulated Release)} - \text{(Spontaneous Release)}}{\text{Maximum Release} - \text{Spontaneous Release}} \times 100$$

EXAMPLE 5

Rapid assay of HIV-specific CTLs Induced by an Immunodominant peptide.

An R15K peptide with the sequence from the HIV gp160 immunodominant V3 loop has previously been identified as a CTL immunodominant epitope in H-$2^d$ mice (Takahashi et al., 1988). In the original studies CTLs, induced in vivo by infecting Balb/c mice with recombinant vaccinia virus expressing HIV env proteins, were shown to lyse syngeneic target cells pre-incubated with R15K. Unfortunately, prior to the present invention, studies in which mice were immunized with free R15K peptide have been reported to be unsuccessful in inducing CTLs (Berzofsky, 1991).

Accordingly, the present inventors sought to examine the induction of CD8$^+$ HIV R15K-specific CTLs in 6–8 week old Balb/c mice by employing differing sites of inoculation, differing forms of the peptide, and recovering the effector cells from different tissue origins. It was observed that draining popliteal lymph nodes (PLN) of mice immunized in the hind-foot pad with 100 µg of the R15K peptide in a 1:1 emulsion with CFA, were the best source of CTL effectors against irradiated (3300 rads) syngeneic target cells preincubated with monomeric R15K (40 µg/ml for 2h at 37° C.). This has particular importance and physiological significance because human lymph nodes have been described as the primary site of HIV replication (Kaneshima et al., 1991; Fauci 1991). An important aspect of this immunization protocol is that CTLs could be recovered by mild homogenization from PLN surgically removed after only 10 days.

To determine the optimal form of the peptide for consistent induction of peptide-specific CTLs in vivo, the R15K peptide was prepared in three different configurations: a) linear monomer, b) disulfide-linked polymer formed by oxidation of cysteine residues added at both the N- and C-termini and c) micelles formed by conjugating the peptide to a dipalmityl-lysine-glycine-glycine at the N-terminus (Hopp, 1984; Sastry & Arlinghaus, 1991). It was found that a single immunization of Balb/c mice in the hind-foot pad with any of the above R15K forms in CFA consistently resulted in generation of CTLs which specifically lysed MHC-matched target cells (P815, H-$2^d$) pre-incubated with the peptide. Such responses were observed in 8 of 12 mice immunized with the monomeric form, in 13 of 13 mice immunized with the micelle form and 6 of 8 mice immunized with the disulfide polymer form of the peptide. Lysis of MHC-matched target cells without peptide pre-treatment (P815) was not observed.

The CTLs induced by all three forms of the peptide also specifically lysed P815 cells infected with a recombinant vaccinia virus expressing HIV gp160 (VPE16), but not cells infected with a control vaccinia virus (P815+VSC8). Western blotting with HIV antibody-positive human sera confirmed the presence of gp160 protein in VPE16-infected, but not in VSC8-infected P815 target cells. The peptide-induced CTLs in Balb/c mice were H-2 restricted. They lysed only peptide pre-treated H-$2^d$ target cells (P815) but not peptide-treated 3A9 target cell, which are expressing the H-2K haplotype. Mice immunized with the micelle, monomeric and polymeric forms of the R15K peptide generated CTLs.

Studies were performed to determine whether the virusspecific CTLs were CD8$^+$ or CD4$^+$. Treatment of the CTL effectors from mice immunized with monomeric peptide with anti-CD8 monoclonal antibodies (MAbs) and rabbit complement abolished the cytotoxicity against peptide treated, or env expressing, targets. In contrast, pre-treatment of effector cells with anti-CD4 MAbs plus complement, or complement alone, had no significant effect. Similar results were also obtained with CTLs generated in mice immunized with the peptide in micelle and polymeric forms. The induction of CD8$^+$ CTLs by R15K is consistent with the use of P815 target cells which express MHC class I, but not class II, gene products (Maryanski et al., 1985). MHC class I-restriction is commonly observed with CD8$^+$ effector CTLs.

Since the CTL epitope studied in the present investigation is in the middle of an immunodominant B-cell active region of the HIV gp120, the B-cell activity of the R15K peptide was investigated. Either as monomer or lipid tailed micelle or after conjugation to KLH, this peptide failed to induce in mice a measurable titer of anti-peptide antibody. However, the mice immunized with peptide conjugated to KLH did make antibodies against KLH, showing that the mice are immunocompetent. Sera from mice immunized in the foot pad were also tested, when it was observed that no anti-peptide antibodies were formed.

Despite the results presented immediately above, the location of R15K in a variable region (V3-loop) of HIV gp160 could be viewed as a reason for not selecting this peptide as a potential vaccine candidate. However, a comparison of gp160 amino acid sequences from 245 different HIV isolates has shown that as little as five different consensus sequences can be defined on a serological basis among all the viral isolates (LaRosa et al., 1990). Therefore, the inventors propose that a cocktail of CTL-inducing peptides from V3-loop regions encompassing all the principal HIV groups (which may be five or less) may be sufficient for generating CTLs specific for cells expressing gp120 from most if not all HIV strains. Such a mixture would then serve as a prototype vaccine for evaluation for prevention of HIV infection of humans.

EXAMPLE 6

Enhancement of Virus-Specific CTL Responses by T helper cell-inducing Peptides.

The present example concerns a method for enhancing the systemic distribution, level of activity, and longevity of virus-specific CTLs induced in response to CTL epitope-bearing-peptides. This method involves the addition of a separate and distinct class of peptides to the immunization mixture that possess T helper cell-inducing activity as a means to enhance the CTL-inducing capacity of a given peptide immunogen.

The inventors method for inducing CTL responses against peptide immunogens, as described in Example 5, results in rapid CTL induction in the proximal lymph node (near the site of injection). However, it was noted that distant lymphoid tissue (i.e. spleen) accumulated a lower level of antigen-specific CTLs. The inventors next reasoned that the further induction of T helper cell activity may be advantageous in improving the dissemination of specific CTLs. As the method described above allows screening of CTL-inducing peptides without the need to include T helper epitope sequences, the inventors tested whether HIV T-cell helper peptides physically mixed with the HIV-specific CTL-inducing peptide R15K would enhance the observed CTL response in mice following multiple subcutaneous (sc) injections. The T helper peptide selected for these studies was C19A which had been previously demonstrated to have T helper cell-inducing activity.

Balb/c mice were injected sc three times at bi-weekly intervals with R15K peptide mixed with the T helper peptide prepared in one of three forms: monomer, lipid tailed and di-sulphide polymer. One week after the last injection, spleen cells were obtained, restimulated and tested for CTL activity. This experiment was successful and significant CTL activity was observed in all the mice. This study was subsequently repeated by injecting mice so with a mixture of R15K and the monomeric form of the T helper peptide and spleen cells were assayed for HIV-specific CTL response after one, two and three sc injections. Here, lower, but significant, level of positive CTL responses were observed.

Prior to the present invention, the R15K peptide by itself had not been shown by any other group to be capable of inducing a CTL response. But the present inventors, as disclosed herein, have demonstrated CTL induction in the popliteal lymph node within 7 days by a single id immunization of Balb/c mice with R15K alone. It was therefore reasoned that a mixture consisting of R15K and the T helper peptide when injected once by the id route might be sufficient to achieve systemic spread and longevity of HIV-specific CTL response.

A number of mice were immunized with a single id injection in the footpads with either the CTL peptide (R15K) alone or in a mixture with the T helper peptide C19A. The results showed that mice immunized with the mixture had substantially higher CTL responses in the spleen than mice receiving just the R15K peptide alone. In addition, the high level of CTL response in the spleen was maintained for up to eight weeks after a single id injection, whilst the helper T-cell peptide injected along lacked CTL-inducing activity.

Lasarte et al. (1992) recently reported that multiple intraperitoneal injections of mixtures of an R15K-bearing CTL epitope and a helper T-cell epitope in mice induced a low level HIV-specific CTL response after three weeks. However, in these experiments, the CTL peptide by itself was not capable of inducing HIV-specific CTLs even after multiple injections. Therefore, the role of T helper peptide in these studies is not clear. On the other hand, the studies described above show that the CTL-peptide possesses the CTL-inducing capacity and the role of T helper peptide is to disseminate and enhance that inherent CTL response of the CTL-peptide. These studies therefore indicate that in order to achieve an efficient, systemic and long lasting cell-mediated immunity, the candidate vaccine preparation should ideally include both T helper and CTL peptides. Another important aspect of this invention is that such a mixture given once intradermally is sufficient to induce a long lasting systemic antigen-specific CTL response.

EXAMPLE 7

Rapid Induction of Influenza Virus- and Sendai Virus-Specific CTLs

The protocol developed for the induction of HIV-specific CTLs, as described above in Example 5, was believed to be generally applicable to the identification, selection and assay of any peptide with unknown epitope specificity, for its ability to prime CTLs in vivo. Accordingly, the in vivo peptide induction of CTLs specific for influenza virus was examined. Deres et al., (1989) had previously shown that a synthetic peptide R⁻, (aa 147–158), corresponding to a portion of the nucleoprotein of influenza virus, could prime influenza virus-specific CTLs in mice in vivo only when covalently linked through the N-terminus to tripalmitoyl-S-glycerylcysteinyl-seryl-serine ($P_3CSS$). However, using the protocol described above, specific $CD8^+$ CTLs, that lysed target cells pre-treated with this peptide, could be induced in vivo by immunization with the free synthetic peptide.

Employing this immunization protocol, an in vivo CTL response was also successfully generated against the unmodified free synthetic peptide (B105: NP 321–336) which represents the immunodominant CTL epitope from the nucleoprotein of Sendai virus. Thus, this method was indeed found to be useful in systems other than those related to the HIV virus. Furthermore, it is believed that this rapid screening method will have medical utility for developing candidate vaccines and therapeutics for various infectious diseases.

EXAMPLE 8

Inhibition of HIV-1 Infection and Syncytia Formation by Human Cells by Synthetic Peptides from gp120.

The present example describes the identification and use of synthetic peptides, derived from gp120, to protect human cells against HIV-1 infection, and to inhibit syncytia formation. MT-4 cells are human T cells that are chronically infected by the human T cell leukemia virus type 1 and undergo lytic infection with HIV-1 (Larder et al., 1989). Therefore, inhibition of HIV-1 infection of MT-4 cells will prevent cell death.

The ability of gp120 derived synthetic peptides to inhibit HIV infection of cells was investigated. Evidence was obtained to demonstrate that synthetic peptides of varying length (8–24 amino acids) selected from the V3 loop of gp120 inhibited HIV infection of both cultured human $CD^+$ T cells as well as freshly prepared primary human $CD^+$ T cells.

It was observed that both the 24 amino acid peptide N24G (aa 308–311) and the 15 amino acid peptide R15K (aa 315–329), with sequences derived from the V3 loop of HIV-1 IIIB, inhibited HIV-1 infection of primary human T cells by 92% at 1 μg/ml (approximately 0.4–0.6 μM) concentration. An 8 amino acid shorter form of the V3 loop peptide, R8K (aa 322–329) also showed 66% inhibition of HIV-1 infection of primary human T cells at 1 μg/ml (approximately 1.25 μM) concentration. Synthetic peptides from V3 loop regions of heterologous isolates, HIV-1 mn (T13Q) and HIV-1rf (H13N) also showed significant inhibition (>60%), each at 1 μg/ml (approximately 0.78 μM) concentration, of cells by the IIIB strain.

A variety of other peptides with sequences derived from the V3 loops of other HIV-1 strains were also found to exhibit significant activity with respect to the inhibition of HIV-1 IIIB infection of human cells. These peptides include D23, D24, D25, D26, D30, D35, D38, D39, D40 and D44, which reflect a variety of strains such as mn, rf, wmj-3, sc, z6, eli, mn (y-1) and mn (y-p). However, it is important to note that this assay was confined specifically to inhibiting the infection of the heterologous strain HIV-1 IIIB. Therefore peptides which did not show activity in this specific assay may still have utility as infection-inhibiting sequences to combat the variety of HIV strains known to be present in the infected human population.

Further studies were conducted to determine the effect of V3 loop synthetic peptides from different HIV-1 strains on syncytium formation. For these studies HeLa CD4 cells were infected with recombinant vaccinia viruses expressing the envelope protein gp160 of HIV-1 IIIB, mn or rf strains, at an m.o.i. of 100, in the presence and absence of V3 loop peptides from respective the HIV-1 stains (i.e., R15K, H13N and T13Q). At 18 hours post infection, cells were observed under microscope, using a magnification of 100, for syncytia.

In these studies, no syncytia were observed in cells incubated with the synthetic peptides before infection with the respective recombinant vaccinia viruses. These results clearly demonstrate the capacity of the V3 loop peptides to inhibit cell to cell spread of HIV-1.

Studies were conducted to examine the stability of the R15K peptide from HIV-1 IIIB isolate in serum. In these studies the R15K peptide was incubated in fetal calf serum at 37° C. and at different time intervals during the incubation aliquots at a final concentration of 1 µg/ml (approximately 0.6 µM) were tested for inhibition of HIV-1 infection of a human T cell line (MT-4 cells). The R15K peptide retained its full strength inhibitory activity for up to 4 hours and 50% of control untreated peptide inhibitory activity was retained even after 24 hours incubation at 37° C. in fetal calf serum.

In addition to the inventors' previous demonstration that the R15K peptide can induce CTL responses (see above, Example 5), they also show this peptide and its analogues from other HIV-i isolates, to efficiently protect human T cells from HIV-1 infection. This activity was demonstrated using cultured cells such as H9, CEM and MT-4 cells, and freshly prepared human T cells. These results indicate that the V3 loop peptides can act in two separate ways: 1) to induce HIV-1 specific cytotoxic T lymphocytes that specifically kill cells expressing HIV-1 gp120; and 2) to prevent infection of normal cells by infectious virus. Thus, these V3 loop peptides have utility not only for vaccines but also as therapeutic reagents to prevent HIV-1 infection in humans or reduce the spread of virus infection in HIV-infected individuals.

EXAMPLE 9

Induction of HIV-specific T cell Responses in Monkeys on Immunization with a Synthetic Peptide Cocktail The present example describes the successful induction of HIV-specific T cell responses in rhesus monkeys with a mixture of eight synthetic peptides, seven of which were derived from conserved regions of the HIV-1 envelope protein. These results, demonstrating the induction of HIV-1 specific T cell responses in a non-human primate model, constitute an important step towards identifying and formulating a synthetic peptide-based vaccine that can induce a broad based cell-mediated immunity for protecting humans against HIV infection.

In the present studies, three rhesus monkeys (#7, #23 and #283C) were immunized subcutaneously with 1 ml (0.1 ml/site) of a mixture of eight synthetic peptides (300 µg of each peptide in sterile water) emulsified in complete Freund's adjuvant at 1:1 ratio. These eight peptides, termed 61, 63, 104, 105, 111, 113, 116 and R15K, had previously been identified as gp160-specific T cell active synthetic peptides. At 3 and 7 weeks after the primary immunization, two booster injections of the peptide mixture (150 µg of each peptide in sterile water) emulsified in incomplete Freund's adjuvant were given to each monkey. Monkey #7 was terminated after 34 weeks, for health reasons unrelated to the study, while the remaining two monkeys (#283C and #23) received one additional booster injection at 25 weeks.

At two week intervals following the first immunization of each animal, 15 ml of whole heparinized blood was collected by venous puncture. The peripheral blood mononuclear cells (PBMC) were separated by standard ficoll-hypaque centrifugation and employed in proliferation assays. The PBMCs were monitored every two weeks for a period of 32 weeks for proliferative responses against individual peptides and recombinant gp160.

It was found that PBMCs from all three rhesus monkeys showed good proliferative responses with peptides 104 (aa 45–55), 111 (aa 118–130) and 63 (aa 519–543); while weak responses were observed with peptides 113 (aa 204–216) and 116 (aa 240–252). Two of the three rhesus monkey-derived PBMC preparations also showed good proliferative responses with peptide 61 (aa 586–598). A significant response was not detected in any of the monkeys with peptides 105 (aa 48–61) and R15K (aa 315–329). PBMCs from all three monkeys showed significantly high proliferative responses with recombinant gp160, the HIV-1 envelope protein precursor, for the entire period of the experiment.

These results demonstrate that mixtures of synthetic peptides from HIV env gene product can prime gp160-specific T cell responses in rhesus monkeys. Because of their ability to induce specific T-cell responses both in mice and rhesus monkeys, these HIV env peptides are proposed to be useful as components of vaccines to prevent HIV infection in humans.

EXAMPLE 10

Mechanistic Analyses and Selection of Candidate Vital Binding and Inhibitory Peptides from CD4.

The present example describes the mechanistic analyses and theoretical concepts employed in the selection of peptide sequences from CD4 for use as potential HIV inhibitory peptides.

The region of CD4 believed to be involved in high affinity binding to gp120 includes the amino acid residues 40–60 (Bates et al., 1989). The corresponding gp120 binding site resides between amino acid residues 402–429 and involves a disulfide bridged loop formed between cysteine residues at position 402 and 429. The present inventors focused on the interaction between these regions of gp120 and CD4 in attempting to develop relatively small CD4-based oligopeptides for use in inhibiting viral infection.

Even though the portion of gp120 believed to interact with CD4 is contained in a fairly well conserved region in the envelope protein, several possible patterns of amino acid sequences were reported to be involved (Lasky et al., 1987). After a careful comparison of amino acid sequence variations of this portion of gp120, the present inventors aligned amino acids that could possibly interact with high affinity with CD4 binding region using standard thermodynamic parameters. The inventors believed this alignment of the CD4-gp120 binding model to be critical in determining the appropriate means of designing oligopeptide molecules to sterically hinder and/or deactivate gp120.

Since the x-ray crystallographic structure of gp120 is not known, the present inventors prepared a two dimensional representation of the CD4-gp120 binding complex (FIG. 1). Using this model they propose that, in spite of variations in the gp120 sequence, selective high affinity binding is possible. In this interaction model, individual binding amino acids of the CD4 and gp120 molecules were arranged to fit in the most thermodynamically favorable fashion. For this the inventors used such parameters like steric hinderance, hydrogen bonding and Van der Walls interactions in order to achieve the maximum binding with minimum free energy.

The first parameter used was an alignment based on minimum steric hindrance. This was accomplished in the case of hypervariable regions of CD4 with small amino acids such as glycine and serine. The examples in the inventors' model of hypervariability coupled with glycine or serine are gp120 positions 413, 424 and 428 binding respectively to CD4 positions S49, G41 and S60. The inventors hypothesized that hypervariable region 426 is between the ends of the CD4 high affinity loop and has little functional binding.

The second parameter to aid in the binding model was a configuration to attain the maximum number of charged salt bridges and hydrogen bonding complexes. In the present model there is only one proposed combination salt bridge-hydrogen bonding complex. This complex is between gp120:K405, Q406 and CD4:D56. Another salt bridge is possible when gp120:410 is an arginine (R) that can interact with CD4:D53. The side chain hydrogen bonding complexes proposed in the constant regions of gp120::CD4 are 403::57, 409::54, 411::52, 412::50, 419::45, 417::46, 410::53. The side. chain-peptide backbone hydrogen bonding complexes are A417::46, 416::47, G425::40, R423::42.

The third and final parameter is side chain hydrophobic Van der Wall interactions. These low energy contact forces involved in the proposed gp120-CD4 complex are maximized by the proposed interaction model. It is predicted that in several instances two gp120 peptides will interact with one CD4 peptide. Some examples of this phenomena are gp120: I408 and I407, 418 and Y419, 421 and 422 that are proposed to interact respectively with CD4: A55, T45 and F43. The proposed individual gp120-CD4 hydrophobic interactions are W411::L51, 414::48, 418::45, 420::44.

Intramolecular gp120 hydrophobic interactions are predicted to be involved in shaping the gross conformation of gp120. There are two predicted areas that are both in proximity to secondary structural bends in the gp120 chain. The isoleucines I407 and I427 near the disulfide bridge are conformationally capable of contacting each other via Van der Walls forces. Similarly I423 and L420 that are near the proline-proline turn are also capable of similar interaction. The complexity of the lock and key interactions predicted above illustrate the ability of the virus to maintain CD4 specificity while still exhibiting mutations of individual amino acids in this region. The use of hypervariable and constant regions coupled with double binding amino acid conformations allow the escape of consistent antibody binding while remain infectious to CD4 bearing cells. Using this gp120-CD4 binding model, the inventors identified potential CD4-based peptides designed to efficiently sterically hinder or deactivate gp120.

In light of the above model, the inventors initially synthesized the CD4 based oligopeptide comprising amino acid residues 40–60, intending to provide an alternate binding substrate so that such an alternate substance once bound would sterically hinder any subsequent cellular CD4 attack by the virus.

Another mechanism of inhibition of viral infection is by the conformational changes that occur as a result of gp120-CD4 complex formation. The inventors propose that conformational changes occur when the two adjacent arginines on CD4 at positions 58, 59 come into contact with the gp120 disulfide bond between amino acid residues 402 and 429. The positive charges on the arginines complex with, and deshield, the electrons on both sulfur atoms of the disulfide bridge. Once the complex is formed it is proposed that the electrons of the sulfur-complexes attack and exchange the acidic protons of the arginines with the cysteine. This attack on the arginines' protons will result in the cleavage of the disulfide bridge. It is proposed that once disulfide bond cleavage has occurred, conformational changes will take place in the gp120-gp41 complex portion of the envelope resulting in the exposure of fusogenic epitope in gp41 to induce fusion of vital surface membrane with the cell membrane.

Following from this, the inventors proposed to prevent such fusion in a therapeutic context by designing an oligopeptide to induce disulfide bond cleavage as well as the associated conformational changes. Accordingly, CD4-based peptides were designed with the aim of inducing premature initiation of conformational changes resulting in the exposure of the fusogenic epitopes in gp41. It is envisioned that the exposure of these epitopes when gp41 is not close to a cellular membrane would result in the deactivation of gp120. This premature deactivation would occur very quickly and easily in the presence of the predicted CD4-gp120 interacting peptides.

EXAMPLE 11

Activity of CD4-Derived Viral Binding and HIV Inactivating Peptides

This example describes the ability of CD4-based peptides, identified according to the above model, to inhibit HIV infection of target $CD^+$ cells, such as human T cells.

After the careful scrutinization of the gp120-CD4 interaction complex described in Example 10, two peptides from the CD4 sequence, C42 (aa 39–60) and C41 (aa 57–60) were selected. These peptides at various concentrations, ranging between 250 ug/ml to 0.001 ug/ml, were pre-mixed with infectious virus. After 30 minutes of incubation at 37° C., the peptide-virus mixture was added onto the monolayer of Hela cells in a petridish and incubated for 7 days at 37° C. At the end of the incubation period the culture medium was analyzed for reverse transcriptase (RT) activity as a measure of virus production. As a negative control an unrelated peptide from the c-mos proto-oncogene was used. Other controls included cells incubated with medium alone or with virus that was not pre-incubated with test peptides.

Figure 2A:
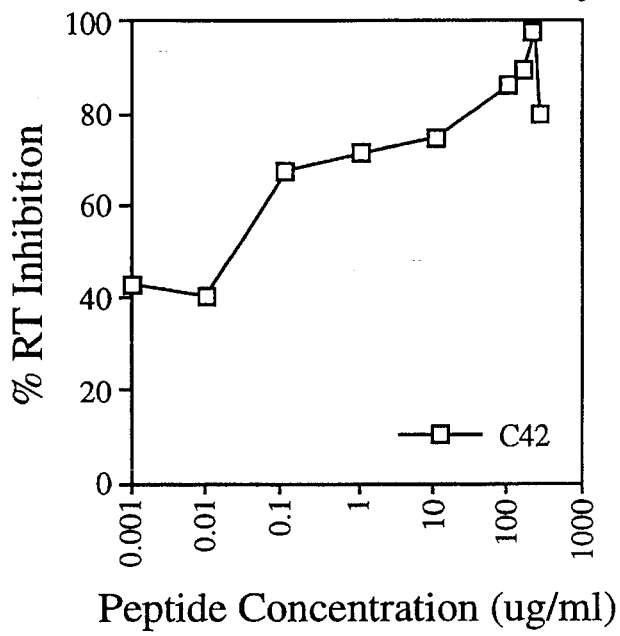
FIG. 2A and FIG. 2B. Inhibition of HIV-1 infection of HeLa cells by CD4-peptides.
Figure 2B:
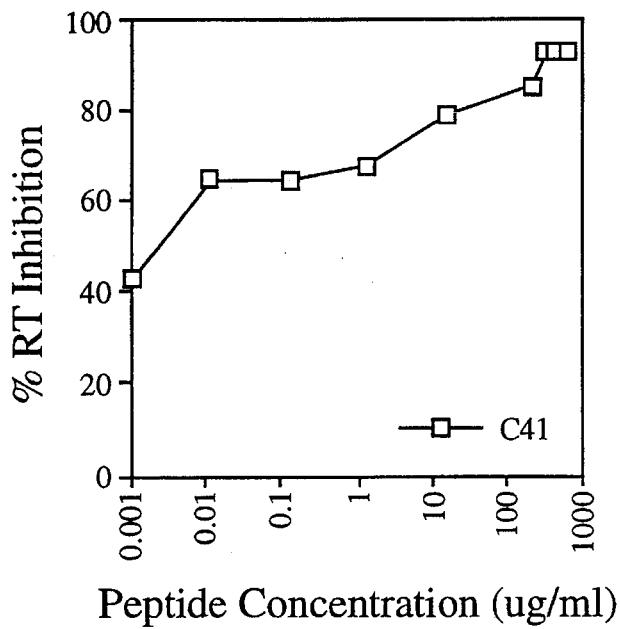

It is clear from the results presented in FIG. 2A and FIG. 2B that cells infected with virus pre-incubated with either C41 or C42 peptides showed significant reduction in RT activity in culture medium. These results indicate that these CD4 peptides inhibited the capacity of the virus to infect CD4-positive human cells. It is particularly important to note that the small tetrapeptide, C41, had inhibitory activity equivalent to that of the larger peptide, C42, 22 amino acids in length.

As discussed above, the actions of the peptides are compatible with the predictions from the inventors' model. It is therefore proposed that the mechanism of anti-HIV activity of these peptides is by either competitive inhibition of the gp120-CD4 interaction (steric hinderance of gp120 binding to CD4 on host cell membrane) or catalytic inactivation of CD4-binding epitopes on gp120.

Several peptide-based anti-HIV formulations have been reported in the literature. CPFs (N-carbomethoxycarbonyl-prolylphenylalanyl benzyl esters) may be the closest in function to the peptides described above (Findberg et al., 1990). The CPF is a dipeptide consisting of phenylalanine and proline that has been esterified with a tert butyl and a benzyl functionalities. The proposed areas within gp120 that this peptide may bind to are all in pockets of non-polarity. The two areas cited by Findberg et al. (1990) are on gp120 at positions W411 and in the proline-proline pocket which corresponds to F43 in the CD4 high affinity binding region.

The tetra-oligopeptide, C41, synthesized by the present inventors bares very few structural similarities to the CPF derivatives reported by Findberg et al. (1990). Even though both reagents were designed to bind to gp120, the areas targeted by each molecule differ considerably. Assuming that both types of molecules bind efficiently to gp120, the proposed mechanisms of inhibition are also different. The CPF's will bind and provide steric hinderance for gp120-CD4 binding (Findberg et al., 1990). In contrast, the peptides of the present invention will not only exert steric hindrance effect but also function to deactivate the virus rendering the virus ineffective for infection.

Another peptide reported in literature to inhibit HIV infectivity is peptide T. Although its HIV inhibitory activity has been disputed, peptide T does appear to activate human monocyte chemotaxis (Marastoni et al., 1988). Peptide T is unrelated to the peptides of the present invention in primary structure.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter and methods can be made and executed without undue experimentation.

REFERENCES

The following references are hereby incorporated by reference for the subject matter as specified in the specification and to the extent that they disclose, teach, enable or provide a basis for various aspects of the present invention.

Arthos et al., Cell, 57:469–481 (1989)
Bates et al., Protein Engineering, 3 (1):13–21 (1989)
Berzofsky, J. A., FASEB J., 5:2412–2418 (1991)
Capon et al., Nature, 337:525 (1989)
Chaudhary et al., Nature, 335:369 (1988)
Click et al. Cellular Immunol. 3:264–276 (1972)
Cohen et al., Science 260(5105):157 (1993)
Deen et al., Nature, 331:82 (1988)
Deres et al. , Nature 342:561–564 (1989)
De Rossi et al., Virology 184:187–196 (1991)
Fauci, A., AIDS Update 4:103 (1991)
Findberg et al., Science 249:287–291 (1990)
Freed & Risser, J. Virol. 61:2852–2856 (1987)
Freed et al., Proc. Natl. Acad. Sci. U.S.A. 87:4650–4654 (1990)
Ghetie et al., Proc. Natl. Acad. Sci. U.S.A., 88:5690–5693 (1991)
Hopp, T. P., Mol. Immunol. 21:13–16 (1984)
Hopp, U.S. Pat. No. 4,554,101,
Houghten, Proc. Natl. Acad. Sci, U.S.A., 82:5131–5135 (1985)
Ibegbu et al., J. Immunol. 142:2250–2256 (1989)
Jameson et al., Science, 240:1335 (1988)
Javaherian et al., Proc. Natl. Acad. Sci. U.S.A. 86:6768–6772 (1989)
Kaneshima, H. et al., Proc. Natl. Acad. Sci. U.S.A. 88:4523–4527 (1991)
Koito et al., Int. Immunol. 1:613–618 (1989)
Kyte & Doolittle, J. Mol. Biol., 157: 105–132 (1982)
Larder et al., Sciehce, 243:1731–1734 (1989)
LaRosa, G. J. et al., Science 249:932–935 (1990)
Lasarte et al., Cell. Immunol. 141:211–218 (1992)
Lasky et al. , Cell 50:975–985 (1987)
Lifson et al., Science, 241:12 (1988)
Linsley et al., J. Virol. 62:3695–3702 (1988)
Marastoni et al., Int. J. Peptide Protein Res., 35:81–88 (1990)
Maryanski, J.L. et al., Eur. J. Immunol. 15:1111–1117 (1985)
McCune et al. , Cell 53:55–67 (1988)
Merrifield, J. Am. Chem. Soc. 85:2149–2154 (1963)
Michel et al., AIDS Research and Human Retroviruses, 8 (4):469–478 (1992)
Millich et al., J. Immunol. 134:4194–4203 (1985)
Murakami et al., Biochem. Biophys. Acta 1079:279–284 (1991)
Rees, Nature, 326:343 (1987)
Robey et al., Proc. Natl. Acad. Sci., U.S.A. 83:7023 (1986)
Sastry, K. J. & Arlinghaus, R. B., AIDS, 5:699–707 (1991)
Takahashi, H. et al., Proc. Natl. Acad. Sci. U.S.A., 8.5:3105–3109 (1988)
Till et al., Science, 242:1166 (1988)
Traunecker et al., Nature, 331:84 (1988)
Travis et al., Virology, 186: 313–317 (1992)
Wain-Hobson et al., Cell 40:9 (1985)
Watanabe et al., Nature, 337:2617- (1989)

What is claimed is:

1. A composition comprising a CD4 peptide of from 4 to 10 amino acids in length including within its sequence the amino acid sequence Ser Arg Arg Ser (seq id no:1), the peptide capable of binding to HIV gp120.

2. The composition of claim 1, wherein said peptide is from 4 to 8 amino acids in length.

3. The composition of claim 2, wherein said peptide is from 4 to 6 amino acids in length.

4. The composition of claim 3, wherein said peptide consists of the amino acid sequence Ser Arg Arg Ser (seq id no:1).

5. The composition of claim 1, wherein said peptide includes within its sequence the amino acid sequence Ala Asp Ser Arg Arg Ser (seq id no:2).

6. The composition of claim 5, wherein said peptide includes within its sequence the amino acid sequence Asp Arg Ala Asp Ser Arg Arg Ser (seq id no:3).

7. The composition of claim 6, wherein said peptide has the sequence the amino acid sequence Leu Asn Asp Arg Ala Asp Set Arg Arg Ser (seq id no:4).

8. The composition of claim 1, wherein said peptide is dispersed in a pharmacologically acceptable vehicle.

9. The composition of claim 1, wherein said peptide is attached to a solid support.

10. A peptide having the amino acid sequence Ser Arg Arg Ser (seq id no:1).

* * * * *

UNITED STATES PATENT AND TRADEMARK OFFICE
CERTIFICATE OF CORRECTION

PATENT NO.    :   5,603,933

DATED         :   February 18, 1997

INVENTOR(S)   :   Victor A. Dwyer, Jagannadha K. Sastry, Ralph B. Arlinghaus, and Pramod N. Nehete It is certified that error appears in the above-identified patent and that said Letters Patent is hereby corrected as shown below:

In column 30, line 6, please delete "Set" and insert therefor --Ser--.

Signed and Sealed this

Twentieth Day of May, 1997

Attest:

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

(A) LENGTH: 4 amino acid residues
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

Ser Arg Arg Ser
 1

(2) INFORMATION FOR SEQ ID NO:2:

(i) SEQUENCE CHARACTERISTICS:
(A) LENGTH: 6 amino acid residues
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:2:

Ala Asp Ser Arg Arg Ser
 1               5

(2) INFORMATION FOR SEQ ID NO:3:

(i) SEQUENCE CHARACTERISTICS:
(A) LENGTH: 8 amino acid residues
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

Asp Arg Ala Asp Ser Arg Arg Ser
 1               5

(2) INFORMATION FOR SEQ ID NO:4:

(i) SEQUENCE CHARACTERISTICS:
(A) LENGTH: 10 amino acid residues
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

Leu Asn Asp Arg Ala Asp Ser Arg Arg Ser
 1               5                   10

(2) INFORMATION FOR SEQ ID NO:5:

(i) SEQUENCE CHARACTERISTICS:
(A) LENGTH: 22 amino acid residues
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

Asn Gln Gly Ser Phe Leu Thr Lys Gly Pro Ser Lys Leu Asn Asp Arg
 1               5                   10                  15

Ala Asp Ser Arg Arg Ser
                20